United States Patent
Stevens et al.

(10) Patent No.: US 7,659,083 B2
(45) Date of Patent: Feb. 9, 2010

(54) DEVICE FOR DETECTING MOLECULES, METHOD FOR DETECTING MOLECULES

(75) Inventors: Fred J. Stevens, Naperville, IL (US); Marianne Schiffer, Downers Grove, IL (US); Priscilla Wilkins-Stevens, Evanston, IL (US); W. Carey Hanly, Chicago, IL (US); Sandra L. Tollaksen, Montgomery, IL (US)

(73) Assignee: Uchicago Argonne, LLC, Chicago, IL (US)

( * ) Notice: Subject to any disclaimer, the term of this patent is extended or adjusted under 35 U.S.C. 154(b) by 0 days.

(21) Appl. No.: 12/199,683

(22) Filed: Aug. 27, 2008

(65) Prior Publication Data

US 2008/0319172 A1 Dec. 25, 2008

Related U.S. Application Data

(60) Continuation of application No. 11/233,913, filed on Sep. 23, 2005, now abandoned, which is a division of application No. 09/368,989, filed on Aug. 5, 1999, now abandoned.

(51) Int. Cl.
*G01N 33/00* (2006.01)

(52) U.S. Cl. .................. 435/7.21; 435/7.1; 435/7.94; 435/70.21; 435/328; 436/501; 436/512; 436/518; 530/300; 530/350; 424/130.1

(58) Field of Classification Search .................. None
See application file for complete search history.

(56) References Cited

OTHER PUBLICATIONS

Pokkuluri et al. (structure, vol. 6, pp. 1067-1073, 1998).*
Padlan et al. (Proceedings of the National Academy of Science, USA vol. 86, pp. 5938-5942, Aug. 1989, Immunology).*

\* cited by examiner

*Primary Examiner*—Lisa V Cook
(74) *Attorney, Agent, or Firm*—Cherskov & Flaynik

(57) ABSTRACT

A construct is provided that is capable of binding a plurality of molecules, the construct comprising a first moiety with a first molecule binding region and a first molecule non-binding region; and a second moiety with a second molecule-binding region and a second molecule-non-binding region, whereby the first binding region and second binding region are at opposite ends of the construct. Also provided is a method for detecting protein having certain amino acid sequences, the method comprising supplying a collection of proteins each with unknown amino acid sequences, contacting the collection with a moiety having a plurality of binding sites capable of binding with the protein having certain amino acid sequences so as to form a moiety-protein complex, and mixing the complex with a marker specific for the moiety in an amount sufficient to indicate existence of the complex.

8 Claims, 3 Drawing Sheets

Solid line: Q38E, dashed line: Rec

DEVICE FOR DETECTING MOLECULES, METHOD FOR DETECTING MOLECULES

The instant application is a continuation application of U.S. patent application Ser. No. 11/233,913 filed on Sep. 23, 2005, now abandoned which in turn was a Divisional of U.S. patent application Ser. No. 09/368,989 filed on Aug. 5, 1999, now abandoned. The complete subject matter of prior applications is incorporated herein by reference in its entirety.

CONTRACTUAL ORIGIN OF THE INVENTION

The United States Government has rights in this invention pursuant to Contract No. W-31-109-ENG-38 between the University of Chicago and Argonne National Laboratory.

BACKGROUND OF THE INVENTION

1. Field of the Invention

This invention relates to an enhanced method and device for detecting molecules, and more specifically, this invention relates to a method and device for detecting the presence of molecules through the manipulation of structural factors which effect dimerization of recombinant antibody variable domains.

2. Background of the Invention

Animals make antibodies in response to the introduction of microscopic substances which are foreign to the host. The antibodies bind these substances and after such attachment, the resulting larger complex is either deactivated or else detected and expelled from the host.

Conventional antibody molecules are used in a wide variety of applications, including detection and diagnostic systems, assays, and treatment protocols. Currently, antibodies are manufactured in the form of polyclonal antisera by immunizing animals and subsequent collection of sera. Antibody proteins also are produced as monoclonal antibodies by lymphocyte/plasma cell culture or as recombinant antibody molecules in bacteria or other cells.

However, all of these various methods are somewhat costly and time consuming. The use of intact antibodies in the above-mentioned detection scenarios has been replaced in part by the use of antibody fragments such as the antigen binding fragment (Fab), which contains the variable heavy domain ($V_H$), one variable light chain ($V_L$) and one constant domain from each chain. Parts of the Fab also have been utilized, including for example, the variable fragment Fv, which consists of $V_H$ and $V_L$ in combination. To date, the Fv has been the smallest functional antibody construct utilized.

There are drawbacks to the use of recombinant antibody fragments in these methods, however. For example, Fv constructs tend to be unstable as $V_H$ and $V_L$ can dissociate from each other, with the $V_H$ precipitating. Also, Fv molecules have only one binding site and are thus monovalent, as opposed to intact antibodies, which are bivalent. As a result of this monovalency, detection sensitivities decrease significantly. Further, the single valence makes Fv molecules unable to cross-link molecules to which they bind. Cross-linkage is important in various medical and biotechnological applications. Substantial effort has gone into constructing linked or bivalent Fvs. See, for example, Hudson P., (1998) Curr Opin. Biotech. 9, 395-403. However, with this substantial effort comes higher implementation costs.

Another disadvantage of current methods is that costs associated with recombinant antibody production are high and reflect the generally low yields of production. Specifically, high production costs of Fv molecules are attributed to the required expression of two genes or the two-gene equivalent as well as the use of artificial polypeptide linkers to connect domains.

A need exists in the art for detecting molecules (e.g. ligands or antigens) with recombinant antibody fragments which, like intact antibodies, are multivalent. The individual detector modules also should be more economical to produce than current detectors.

SUMMARY OF THE INVENTION

It is an object of the invention to provide an enhanced method and device for detecting molecules that overcomes many of the disadvantages and limitations of the prior art.

Another object of the present invention is to provide a device for detecting molecules which is small in size yet retains the multivalent binding capabilities of an intact antibody. A feature of the invented device is that it is relatively the same size as an Fv, but it is bivalent. An advantage of the invented device is that its bivalency provides a functional increase of affinity per unit mass as compared to a typical antibody fragment such as Fv and gives the invented device the capability to cross link molecules.

Still another object of the present invention is to provide a device for detecting molecules which is more economical to produce than currently available detection devices. A feature of the invented device is that it is composed of two copies of the expression of only one gene. An advantage of the invented device is that expression of only one gene is more economical than the expression of two genes.

Briefly, the invention provides for a molecule with two ligand binding sites, A molecule with two antigen binding sites, the molecule comprising a first light chain variable domain having a first end terminated by a first amino moiety and a second end terminated by a first carbonyl moiety; and a second light chain variable domain having a first end terminated by a second amino moiety and a second end terminated by a second carbonyl moiety, whereby the second light chain variable domain is juxtaposed to the first light chain variable domain so that the first amino moiety and second amino moiety are counterpoised.

The invention also provides a molecule capable of binding a plurality of ligands, such as antigens, the molecule comprising a first moiety with a first antigen binding region and a first antigen non-binding region, and a second moiety with a second antigen-binding region and a second antigen-non-binding region, whereby the first binding region and second binding region are at opposite ends of the molecule.

The invention provides a method for detecting protein having a certain amino acid sequence, the method comprising supplying a collection of proteins, contacting the collection with a moiety having a plurality of binding sites, or a unique binding site, capable of binding with the protein having the certain amino acid sequence so as to form a moiety-protein complex, and mixing the complex with a marker specific for the moiety in an amount sufficient to indicate existence of the complex. This method also can be performed by contacting the collection with a library or second collection of binding molecules.

The invention also provides a molecule capable of serving as a skeleton for the incorporation of additional structural changes. Such changes will result in a plurality of devices, each of which binds a particular ligand such as an antigen.

BRIEF DESCRIPTION OF THE DRAWING

The present invention together with the above and other objects and advantages may best be understood from the following detailed description of the embodiment of the invention illustrated in the drawing, wherein.

DETAILED DESCRIPTION OF THE INVENTION

Figure 2:
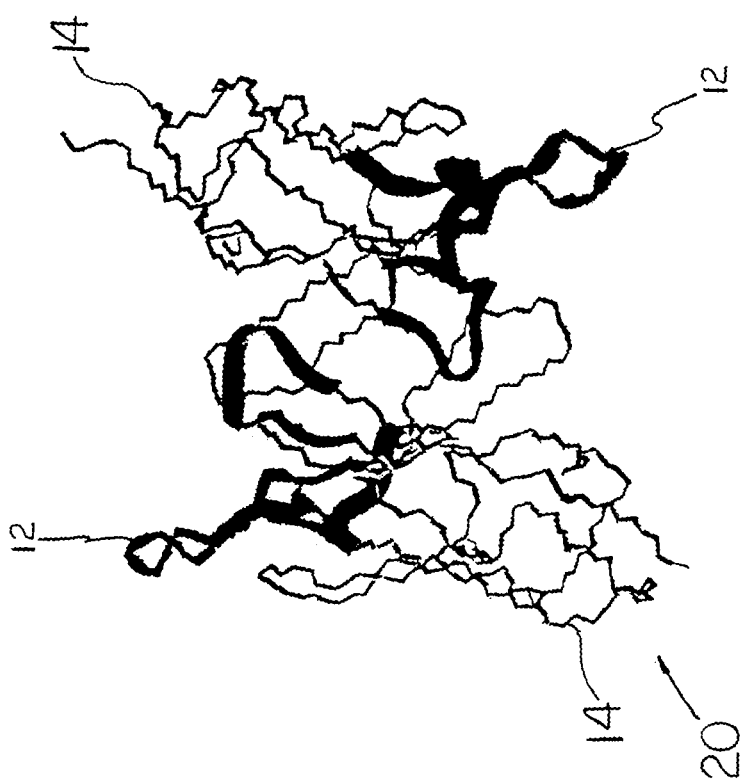
FIG. 2 is an x-ray crystallographic depiction of a bivalent detector molecule, in accordance with features of the present invention.

Generally, the invention is an antigen detector that provides bivalent capability. The detector is the result of the joining or polymerization of recombinant antibody subunits. Specifically, the new synthetic construct derives its bivalency from its being comprised of a dimeric assembly of two single light chain variable regions. The inventors have labeled these constructs "Janusbodies" after the Roman deity Janus who had two faces looking in opposite directions. The name is apropos inasmuch as the binding portions of the construct, or the variable regions of each of the light chain variable regions, are counterpoised or otherwise situated at opposite ends of the construct. This arrangement allows for binding of two molecules, such as two ligands or antigens, to the same construct.

In light of this two-molecule binding functionality, the amount of synthetic construct necessary to bind or detect an epitope is roughly half the amount required of Fv constructs at the same detection level. As such, the bivalency imparts an increase of functional affinity per unit mass.

Another advantage of the bivalent nature of the synthetic construct is that it provides the capability of cross-linking molecules to which it binds. As such, these synthetic molecules mimic hormones whose functions are mediated by cross-linking specific cell surface receptors. The cross-linking ability of the bivalent structure could also be exploited to mediate agglutination of targeted molecules so that they may be simultaneously concentrated and removed from solution during filtration procedures.

As more fully disclosed infra, the invented constructs exhibit up to 1,000 times the thermodynamic dimerization stability seen in naturally-occurring variable light chain dimers, such as Bence-Jones proteins.

The inventors have determined that their invented bivalent structure is viable through a four-step process: First, an unnatural mechanism was developed for dimerizing light chains which results in placing two identical binding sites at opposite ends of the resulting dimer. Essentially, this mechanism embodied "flipping" the domain as a consequence of a single amino acid substitution. Specific, single site-mutations are identified and discussed infra.

Second, a means was developed to increase the stability of the association of the light chain variable domains to create a durable, functional dimer. A number of variants have been developed (See Example 2, infra) in which a hydrophobic residue introduced by mutation is buried by dimer formation, resulting in two-to-three orders of magnitude increased affinity between the dimer subunits.

Third, a means to increase the thermodynamic stability of the variable domain components of the dimer was devised so as to increase the shelf-life of the molecule and to allow structural changes in normally invariant sites to create dimers of diverse binding capabilities. Three concurrent amino acid substitutions were devised and introduced to increase the protein monomer folding or thermodynamic stability by a factor of 1,000. This increase in monomer stability allows for the manipulation of the exposed or molecule-binding surfaces of the monomer without danger of unfolding.

Fourth, the invented construct has the potential to bind to a myriad of molecules. Essentially, anti-western blot techniques have been utilized to demonstrate the construct's activity. Specifically, while an array of "unknown" proteins are scrutinized by a single probe of known specificity (i.e., an antibody) in Western blotting, the inventors have instead subjected an array of known proteins, or fragments or mutants of proteins, to mobile probes of unknown specificity comprising the invented Janusbodies, either singly or as a library of Janus bodies. In this manner, Janusbodies of a given specificity can be identified. The result is a library of diverse molecules which can identify many proteins.

An advantage of the utilization of the invented Janusbodies is that the constructs impart a functional increase of affinity per unit mass. For example, when comparing a Janusbody (12,000 Daltons) to an Fv (25,000 Daltons) with an identical binding site, the molecule with two binding sites has the higher probability of binding. Thus, the Janusbody can be used in any current or future application of Fvs, with equivalent effectiveness at lower concentration.

Figure 1:
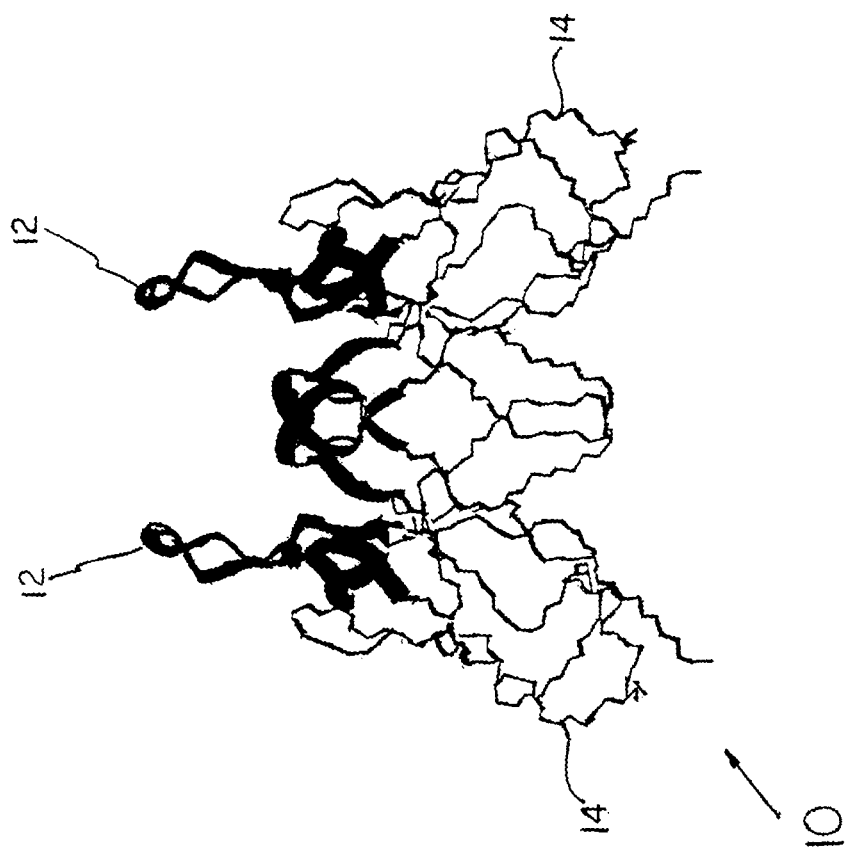
FIG. 1 is an x-ray crystallographic depiction of a typical light chain variable domain dimer.

A comparison of a typical light chain dimer and the engineered dimer is depicted in FIGS. 1 and 2. FIG. 1 depicts a typical light chain dimer generally designated as numeral 10. FIG. 2 depicts the engineered dimer, generally designated as numeral 20. As depicted in FIG. 1, the complementarity determining regions (CDR) 12, depicted in bold, are juxtaposed, whereas in the bivalent moiety (FIG. 2) the CDRs are situated at generally opposite ends or poles of the construct. Similarly, the framework regions 14 of typical light chain dimers are adjacently positioned, compared to the counterpoised configuration seen in the engineered construct. Variation of the amino acid sequence of the CDRs and FR regions leads to different molecular binding specificities. Indeed, manipulation or substitution of CDRs of thermodynamically stable monomer subunits results in conferring binding capability to different monomer "backbones."

Generally, the invented construct is composed of two copies of the expression of only one gene. The invented construct differs from the usual spontaneously self-associating domains found in nature in that the complementarity determining segments (CDRs) are positioned at opposite ends of the dimeric assembly. As such, the CDR segments of each subunit are paired with "framework" (FR) portions of the domain to form stable duplexes. This results in very stable antigen binding surfaces which are comparable in size to that of an antibody. This contrasts with a natural tendency for single gene antibody variable domains to transiently associate into configurations. Such natural associations resemble the configurations of dimers composed of VH and $V_L$ domains (i.e., with CDR regions of one domain juxtaposed to CDR regions of the other domain). However, most of these natural associations last for only brief periods of time (one to a few seconds) and thus are not stable or amenable for development into useful binding reagents.

Figure 3:
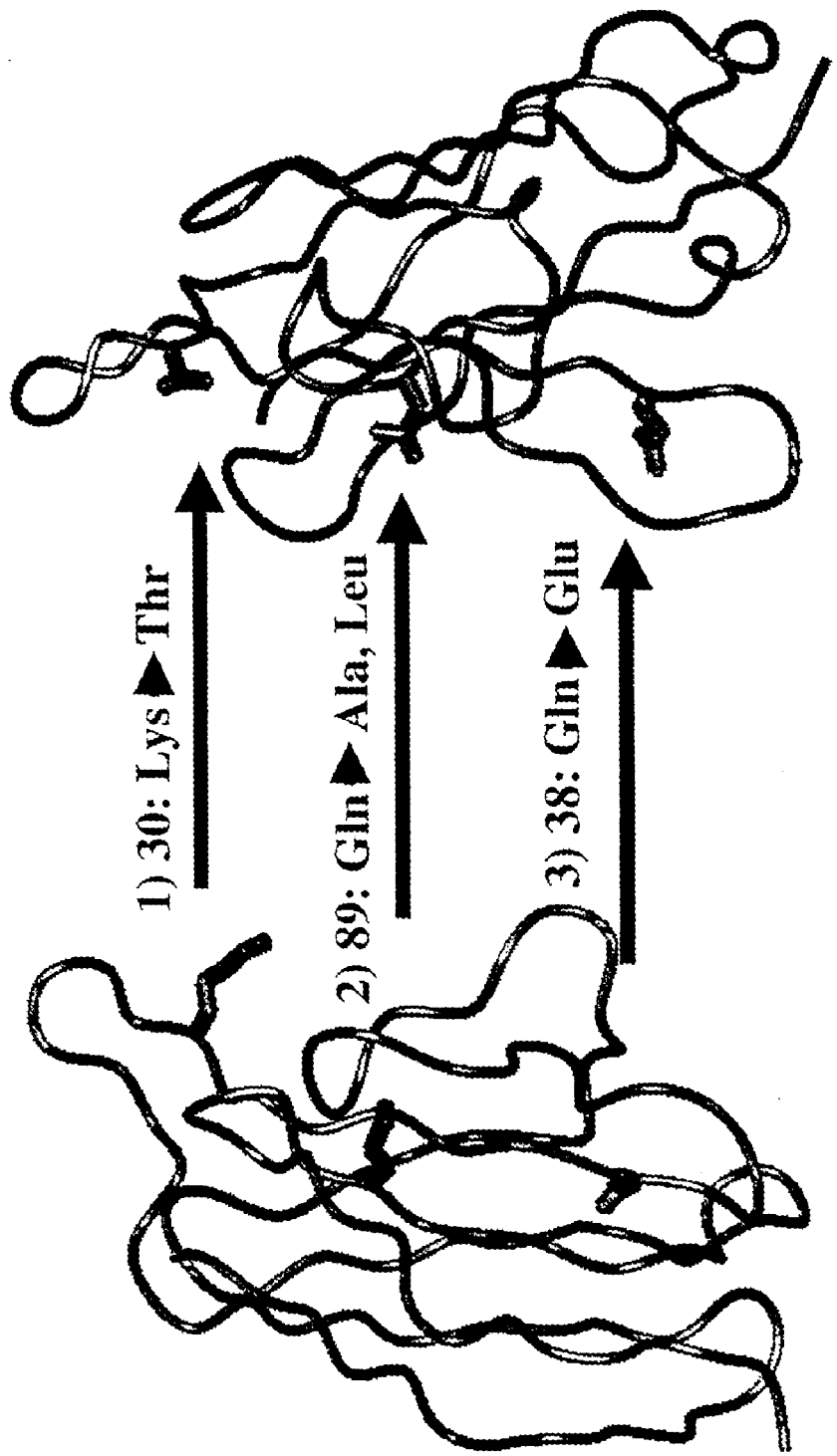
FIG. 3 is an x-ray crystallographic depiction of a subunit of a light chain variable dimer illustrating the positions and substitutions of three amino acid residues.

The inventors have developed the means to engineer the counterpoised effect by introducing amino acid substitutions at one or a plurality of sites. These substitutions define binding sites for target molecules. One result is that a plurality of target molecules can be linked via the same Janusbody construct. Exemplary amino acid substitutions are depicted in FIG. 3, with native "Len" depicted on the left and "Len" with three potential mutations depicted on the right. Specifically, Lysine 30 is replaced by Threonine, Glutamine 89 is replaced by Alanine or Leucine, and Glutamine 38 is replaced by Glutamic Acid. More thorough detail of effecting domain flips in immunoglobulin molecule subunits so as to place two identical binding sites at opposite poles of dimers is found in Pokkuluri et al. *Structure* 6: 1067-1073 (Aug. 15, 1998) and incorporated herein by reference.

As noted supra, any one of the three substitutions results in a domain flip. However, the inventors have found that the Glutamine 89 to Leucine substitution results in a dimer that is between 800 and 1000 times more stable than what results from a substitution at either of the other two positions. The inventors have determined that replacement of the buried polar residue (carbonyl on Glutamine) with a hydrophobic residue (such as those found in Alanine and Leucine) promoted increased dimer stabilization. Surprisingly and unexpectedly then, the inventors have found that the elimination of unsatisfied polar residues, results in a flipped dimer that has high stability.

The inventors also have found that a double mutation of "Len", specifically a Gln89Leu+Gln38Glu construct, results in a dimerization constant that is more than 1000-fold greater than the dimerization constant for native "Len".

The relative orientation of one $V_L$ domain with respect to the other is altered by ~180 degrees; the same surface of the monomer is involved in the interface of each protein. The two-fold axes relating the dimers in the two types of structures differ by ~90 degrees in their orientations. The strands of the monomers are approximately parallel to the long axis of the interface, but they are perpendicular to the two fold axis between them. To convert to the flipped dimer, one of the monomers would be required to rotate ~180 degrees around an axis oriented ~90 degrees to the original two fold axis.

Construct Selection Detail

A system for selecting constructs having desired molecular recognition properties has been developed. This system is a modification of the phage display techniques, as described by Rodi et al., *Curr. Opin Biotechnol*. (1999) 10, (1) pp 87-93; Koscielska et al., *Acta Biochim Pol*. (1998) 45(3) pp 705-20, Siegel et al. *J. Immunol Methods* (Aug. 7, 1997) 206 (1-2) pp 73-85, and Mersmann et al., *J Immunol Methods* (Nov. 1, 1998) 220 (1-2) pp 51-8, all of which are incorporated herein by reference. Briefly, diverse single chain antibody domains are screened for binding to a particular antigen by first varying the DNA encoding the CDRs of a single chain antibody. Then the variant is subcloned into a minor coat protein of a phage (for example, gene III of bacteriophage f1) to produce a chimera to be displayed on the phage's outer surface. A battery of so modified phages are then exposed to the target antigen, with the desired phage finally determined through affinity chromatography.

In this invention, phage-display methodology is utilized in a way similar to that in which analogs of single-chain Fv genetic constructs are synthesized. In single chain Fv construct synthesis, a copy of a VH gene and a copy of a $V_L$ gene are connected by a long linker peptide and then replicated using a phage vector.

To produce the bivalent construct, such a construct first has to be chosen via phage display. As such, in any construct candidate, a peptide linker joins the C-terminus of one $V_L$ gene to the N-terminus of a second $V_L$ gene. This is to assure that any phage-displayed construct retains the dimeric features of the construct. Without the linker, bulky macromolecules (such as fusion proteins) which contain suitable $V_L$s may prevent dimerization from occurring. The bivalent construct displayed on the surface of phage is functionally monovalent, inasmuch as the attachment of the construct to the phage protein blocks one of the binding sites.

Although the prototype construct would contain two genes that encode the same amino acid sequence for both $V_L$s, the synthetic genes would be different at the DNA level to maximize stability (i.e., prevent homologous recombination and deletion of one of the genes). In general, the third base of a number of codons would be varied for one of the genes. This would disrupt gene identity while preserving amino acid sequence of the encoded polypeptide.

A library of bivalent genetic constructs are developed by generating CDRs via polymerase chain reactions and then randomizing or combining them with FRs to form domains. The bivalent construct is then further optimized by subsequent rounds of random genetic variation and selection, or by protein engineering guided by crystallographic analyses of the construct or of complexes formed with antigen, or by molecular modeling of the construct or complexes.

After final selection, the DNA sequences of the two $V_L$ genes are determined. At this juncture, the phage expression construct (comprising the linker flanked with $V_L$ genes) has served its purpose. A recombined gene is produced, incorporating the CDR and FR components which were originally dispersed between two gene segments. A plasmid expression construct is produced with the $V_L$ gene representing the recombinant construct. Upon expression, the $V_L$ domain dimerizes, inasmuch as the FR has the appropriate mutations to do so.

The specific light chain variable domain utilized in the following examples has been designated "Len". In the case of this protein, the formation of the flipped dimer is thought to be prevented by two independent factors: (1) Excess positive potential at the interface, and (2) an unpaired polar residue that would be buried at the interface.

"Len" has been chosen for its stability as a monomer, inasmuch as it has the stability, expression and appearance characteristic of a Bence-Jones protein. In light of the foregoing, however, any stable substructure (i.e., any stable framework region) can be utilized as a foundation for modifying CDR portions of the subunits. Aside from "Len", other suitable and well characterized $V_L$ structures include "Rec", "Jto", "Wil", "Loc", "Wat", "Cle" and "Rhe." These proteins are the products of typical expression constructs, the development of which was funded by the U.S. National Institutes of Health and the U.S. Department of Energy. As such, either the proteins and/or the constructs for generating the proteins are widely available at government laboratories, such as Argonne National Laboratory, in Argonne, Ill. The structures for these various proteins are available at the government branches listed above and/or at the PROTEIN DATA BANK, operated by The Research Collaboratory for Structural Bioinformatics (RCSB). RCSB Mirrors include Rutgers University in New Jersey, the San Diego Supercomputer Center at the University of California in San Diego, Calif., and the National Institute of Standards and Technology (Gaithersburg, Md.), which is a non-regulatory branch of the U.S. Department of Commerce's Technology Administration, Washington, D.C.

Figure 4:
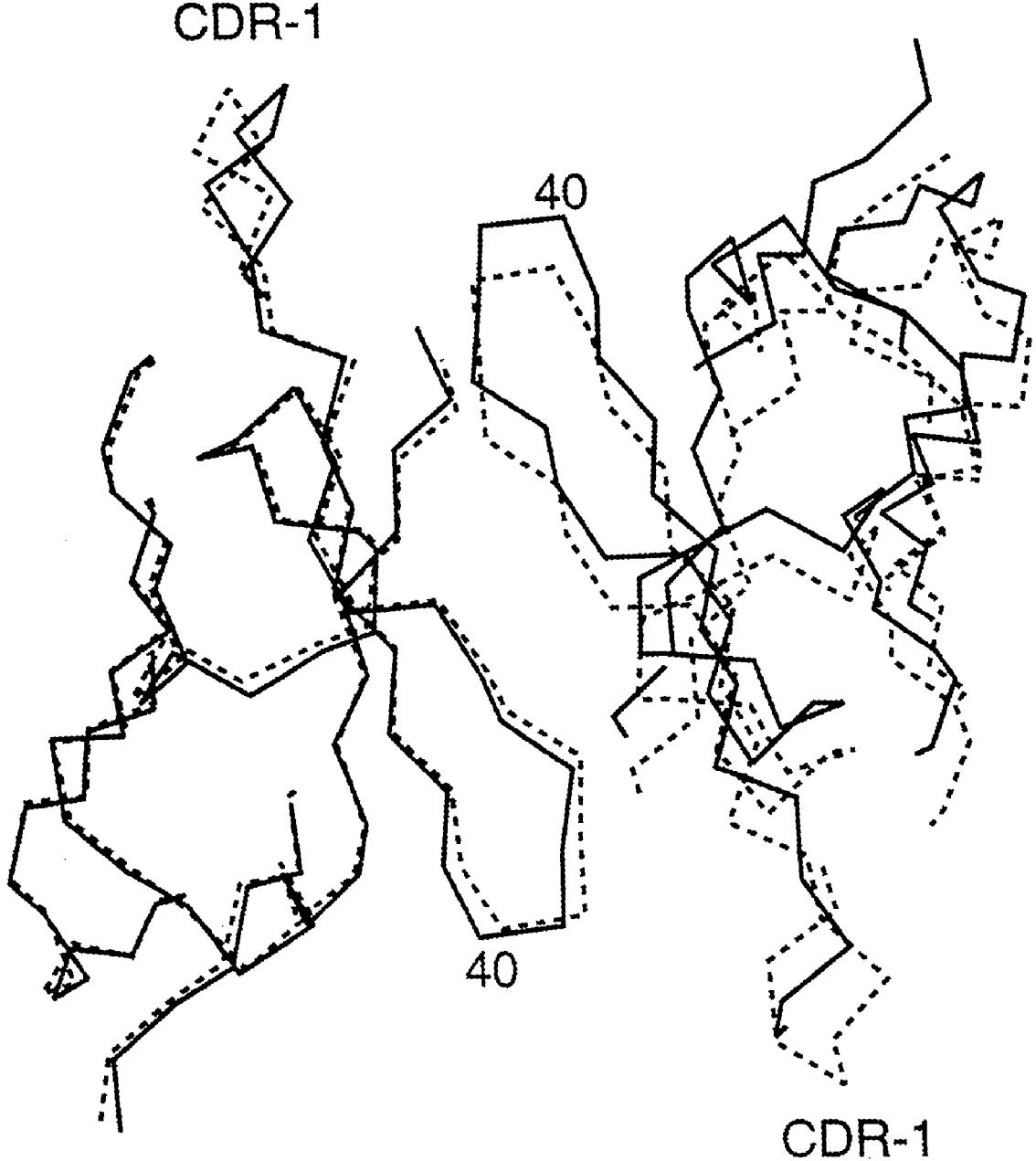
FIG. 4 is a computer generated depiction of two pairs of counterpoised $V_L$s, in accordance with features of the present invention.

Some of the structures are very similar to each other. For example, and as depicted in FIG. 4, constructs utilizing "Len" and "Rec" as foundation structures having a Gln38Glu substitution are nearly superimposable.

The protocol for "Len" isolation and a morphological characterization of "Len" is disclosed in Pokkuluri, et al., discussed above, and Raffen, et al. *Protein Engineering* 11 No. 4, pp. 303-309 (1998), both papers incorporated herein by reference.

Example 1

In this example, the mutations were created via electrostatic manipulation of the interface. Specifically, subunits were created having charged residues to reduce excess positive potential at the interface of the joined monomers. Flipped dimers were formed by either the addition of a negatively charged residue or the removal of a positively charged residue.

When single-site mutants were formed on identical light chain variable domains, the modified domains formed "flipped" dimers in which one domain was rotated by about 180° compared with the native protein. Dimers of the native protein resemble dimers formed between the variable domains of the Fab immunoglobulin fragments.

The engineered dimer exhibited higher thermodynamic stability compared to the native protein dimers, primarily due to the fact that the engineered dimers had more interface surface area (i.e., surface area that was buried from ambient solvent). Also, more hydrogen bonds and salt bridges were formed between the modified monomers. In general, native protein is not found in the flipped-domain dimer configuration inasmuch as such a juxtaposition would result in excessive positive electrostatic potential at the dimer interface.

Two of the sites that were manipulated, singly, to form stable "flipped" or counterpoised structures are Gln38 to Glu38, and Lys30 to Thr30. In the first instance Gln38 is a conserved (i.e., found in most human $V_L$ genes) residue that forms symmetrical hydrogen bonds across the dimer interface. The inventors surmise that when neutral glutamine (Gln) 38 was replaced by the negatively charged glutamic acid (Glu) residue, a flip occurred, due to the excess negative charge at the modified site. Likewise, when positively charged Lysine (Lys) 30 was replaced by threonine (Thr) excess negative charge also caused a flip.

The association constant ($K_a$) of a flipped domain dimer which is the result of the Gln38 to Glu substitution is $5.8\times10^5$ $M^{-1}$. The $K_a$ of the flipped dimer which is the result of the Lys30 to Thr substitution is $0.8\times10^5$ $M^{-1}$ These $K_a$ values are of the same order of magnitude as the $K_a$ ($2\times10^5$ $M^{-1}$) for the native "Len" (conventional dimer) and significantly less than the $K_a$ values of the Gln89Ala mutant ($4\times10^6$ $M^{-1}$) and the Gln89Leu mutant ($>10^8$ $M^{-1}$). When the mutations are combined, as noted supra, enhanced association occurs. For example when the two mutations Gln89Leu+Gln38Glu are present in the same construct, $K_a$ on the order of approximately 1000-fold higher than that seen in native "Len" occurs.

Increased dimer stability results, even in the presence of a buried polar residue.

To demonstrate that the invented bivalent constructs do in fact bind with other molecules, the anti-Western or reverse blotting technique noted supra, was employed.

Several variants of Bence Jones light chains were utilized to visualize distinctly different tissues (distinct from their two-dimensional gel electrophoresis pattern). Specifically, mouse liver proteins and human serum proteins were selected.

The multivalent constructs were biotinylated using a commercially prepared kit, such as EZ-Link Sulfo-NHS-LC-Biotinylation Kit available through Pierce, in Rockford, Ill. Biotin is a low molecular weight vitamin found in tissue and blood, and since it is a relatively small molecule, it can be conjugated to many proteins without altering their biological activities. The biotin tag provides the basis for visualization of the construct-protein complex on a blot. Visualization involves a subsequent reaction of the biotin with avidin (a basic glycoprotein) or an avidin variant, conjugated to a chemical capable of generating a chemiluminescent product. Avidin contains four subunits, each comprised of 128 amino acids. It is very soluble in water and salt solutions and is stable over a wide range of pH and temperatures. Neutravidin is similar to avidin but this avidin variant has no carbohydrate and has a more neutral isoelectric point. It is also resistant to dissociation from the neutravidin-biotin complex, and also, the four subunits of neutravidin are resistant to dissociation from each other.

The avidin (or-neutravidin)-biotin interaction is the strongest known noncovalent biological recognition between protein and ligand. The bond forms rapidly and is unaffected by extremes of pH, solvents and other denaturing agents. It is this combined product (i.e., the avidin-biotin complex) that was used in the detection of the invented constructs that have reacted to tissue proteins. Detection was done using commercial Chemiluminescent Kits (e.g., the Chemiluminescence Blotting Substrate [POD]™) by Boehringer-Mannheim, Germany.

After the two-dimension electrophoresis 2DE gels of serum or mouse livers were run, the proteins were transferred from the gels to more resilient substrates via typical blotting processes. Typical substrates include nitrocellulose membranes, nylon membranes, and diazobenzyloxymethyl paper. The inventors employed polyvinylidene difluoride (PVDF) membranes for such transfers, via a commercial Semi-Transfer apparatus (Semi-Phor TE70) by Hoefer Scientific Instruments, San Francisco, Calif. The membranes were first blocked overnight at 4° C. in 1 percent blocking solution, to block any nonspecific protein binding to the membrane. The blocked membranes were then incubated for two hours at room temperature with the primary antibody, which in this case is the biotinylated construct diluted in 0.5 percent blocking solution.

The membranes were then washed twice in a solution of TBST, Tris buffered saline containing Tween (0.1 percent), a detergent. Subsequently, development of the blots to identify sites of interaction of the biotin-labeled primary antibody was carried out according to the manufacturer's directions with a commercially available Chemiluminescence blot-development system designed around peroxidase-labeled neutravidin, the conjugate. Ultimately, the processed membranes were exposed to X-ray film to obtain a visual record of sites of interaction of the primary antibody with the array of proteins on the membrane.

More specifically, the blotting occurred as follows: After washing with TBST, the membranes were then re-equilibrated twice for 20 minutes each time in blocking solution, to prepare for the introduction of the secondary reagent, which was Neutravidin/horseradish peroxidase conjugate-prepared in 0.5 percent blocking solution. The membranes were incubated at room temperature for one hour. Finally, the membranes were washed four times in TBST solution, for 15 minutes each time.

Next, the development step was performed for visualization of the reaction according to the manufacturer's directions. The Chemiluminescence blot/development system used is designed around a peroxidase labeled secondary reagent (the neutravidin/horseradish peroxidase conjugate noted above). The peroxidase, in the presence of hydrogen peroxide, catalyzes the oxidation of diacyl hydrazides like luminol. An activated intermediate product that forms emits light as it decays to the ground state.

The light emission (which exposes X-ray film) is enhanced by an additional chemical, 4-iodophenol, which acts as a radical transmitter between the formed oxygen radical and luminol. This detection system is as sensitive as radioactive detection methods. Membranes were developed in the luminol chemicals for 1-3 minutes each, then drained, put in between plastic sheets, wiped off, and exposed to X-ray film in a flat cassette holder for 1 to 3 minutes, and processed in the X-ray developer machine.

Example 2

The inventors found that increased interface surface-area resulting from flips does not necessarily indicate increased levels of hydrogen bonding. This became particularly evident when the inventors found that candidate atoms of some buried side chains are not in appropriate positions with adjacent moieties to form hydrogen bonds.

In this example, the inventors found that the mode of dimerization of a $V_L$ domain with β-sheet structure also can be changed to a flipped configuration but without changing the electrostatic nature of the interface. Specifically, the inventors replaced a buried polar residue by a hydrophobic one to arrive at the flipped or counterpoised dimer quarternary arrangement seen in Example 1. As noted supra, a myriad of suitable substrates (e.g., FR-modified $V_L$ domains) can be utilized on to which CDR's are grafted or for which CDR mutants are generated. In this example, the $V_L$ protein "Len" was utilized, with the Q89→A (Glu89→Ala) and the Q89L (Glu89→Leu) mutants being constructed, expressed and purified as described in Wilkens Stevens, et al. *Protein Sci* (1995) 4 pp 421-432, and incorporated herein by reference.

In conventional $V_L$ domain dimers, Gln89 is partially exposed to the solvent (e.g. human d4 light chain "Len") and it interacts with Tyr 36 of the same monomer (human κ4 light chain "Len") and with Tyr 36 or Gln89 of the partner or opposing monomer across the dimer interface. In flipped dimers, both Tyr36 and Gln89 are buried. Tyr 36 interacts through a water molecule with the backbone carbonyl oxygen of proline 44 of the other monomer. However, with regards to the Gln89, its Nε2 atom does not have suitable neighbors for formation of hydrogen bonds. When Gln89 of the native "Len" $V_L$ is replaced by Leu, the hydroxyl group of Tyr36 still forms an H-bond with the carbonyl oxygen of Pro44. Leu89 is in van der Waals contact with the same residues as Gln89 in the flipped configuration. The Gln89 to Leu substitution results in a tight packing of the dimer interface. The results of the Leucine substitution illustrate that the substitution of a larger hydrophobic residue not only facilitates a flipped dimer configuration, but also significantly increases the dimerization constant of the resulting construct. Indeed, the dimerization constant for the Gln89Leu mutant (flipped domain dimer) is greater than $10^8$ $M^{-1}$, which is significantly higher than the dimerization constant for the conventional dimer of unmutated "Len."

When Gln89 is replaced by Alanine, rearrangement of the dimer interface results in a smaller cavity (61 $Å^3$ in the case of Alanine substitution versus 77 $Å^3$ when Gln is present). $K_a$ of this mutant is $4\times10^6$ $M^{-1}$. This collapse of the cavity results in a change of relative positions of a number of atoms, including Try36 and Pro44. As such, a single amino acid change of this type affects the overall stability of the dimer inasmuch as the overall stability of the dimer is affected by both the attractive forces and the repulsive forces of juxtapositioned atoms. Also as a result of the Alanine substitution, the Tyr36 of each subunit forms a direct hydrogen bond (as opposed to H-bonding through the water intermediary seen with Leu substitution) with the carbonyl residue of Pro44.

In summary, the inventors found that protein-protein interactions are enhanced by replacement of residues having unsatisfied H-bonds with hydrophobic residues. Conversely, replacement of buried hydrophobic residues by "unsatisfied" polar side chains may be an approach to decrease, but still maintain, subunit interactions of high affinity, multi-subunit protein complexes. As such, dimer stabilization is effected by manipulation of either or both electrostatic characteristics or steric hindrance phenomena.

While the invention has been described with reference to details of the illustrated embodiment, these details are not intended to limit the scope of the invention as defined in the appended claims. For example, the invention makes it possible to modify a $V_L$ domain in some solvent-accessible FRs that normally do not participate in antigen binding, such as a region on the $V_L$ molecule that is opposite the CDRs and embodies the loops between the beta strands. In a Janusbody, some of those loops on the carboxyl-terminal side of one domain are in close proximity to the CDRs of the partner domain. Modification of these loops would enhance the binding affinity of the Janusbodies.

The invention claimed is:

1. Synthetic constructs comprising:
    a) a moiety having a plurality of binding sites, wherein the moiety is a dimer of identical Bence Jones domains-;
    b) a surface of each domain forming an interface between the domains, each surface containing an amino acid substitution at position 38 and/or position 89, whereby the domains are flipped from their native configuration such that the surfaces still define the interface; and
    c) each domain comprising a variable region wherein the variable regions of the domains are situated at opposite ends of the dimer such that the complementarity determining region of each domain is paired with the framework portion of each domain.

2. The construct as recited in claim 1 wherein the moiety is between 20,000 daltons and 30,000 daltons.

3. The construct as recited in claim 1 wherein the binding sites are at opposite ends of the moiety.

4. The construct as recited in claim 1 wherein the flip positioning of the $V_L$ domains occurs when single site mutants exist on each of said domains.

5. The construct as recited in claim 1 wherein the flip positioning of the $V_L$ domains exists when position 38 is substituted.

6. The construct as recited in claim 1 wherein the flip positioning of the $V_L$ domains exists when position 89 is substituted.

7. The construct as recited in claim 1 wherein the flip positioning of the $V_L$ domains exists when positions 38 and 89 are substituted.

8. The construct as recited in claim 1 wherein the domain is a variable light chain selected from the group consisting of Len, Rec, Jto, Wil, Loc, Wat, Cle and Rhe.

* * * * *